US00PP09737P

United States Patent [19]

Hilverda

[11] Patent Number: Plant 9,737

[45] Date of Patent: Dec. 10, 1996

[54] CARNATION PLANT NAMED HILDISCO

[75] Inventor: Jan J. Hilverda, De Kwakel, Netherlands

[73] Assignee: Messick Company, Saratoga, Calif.

[21] Appl. No.: 526,239

[22] Filed: Sep. 11, 1995

[51] Int. Cl.[6] ..... A01H 5/00

[52] U.S. Cl. ..... Plt./70.2

[58] Field of Search ..... Plt./70.1, 70.2

*Primary Examiner*—James R. Feyrer

*Attorney, Agent, or Firm*—Proprietary Rights International

[57] ABSTRACT

A distinct cultivar of Carnation plant named Hildisco, characterized by its medium pink petal color with contrasting dark rose pink eye; compact growth habit; freely branching plant habit, uniform inflorescence display; and numerous flowers per plant.

1 Drawing Sheet

The present invention relates to a new and distinct cultivar of Carnation plant, botanically known as *Dianthus caryophyllus,* and hereinafter referred to by the cultivar name Hildisco.

The new cultivar is a product of a planned breeding program conducted by the inventor in Aalsmeer, Holland. The objective of the breeding program was to create new potted Carnation cultivars having more rapid growth and different or more vivid flower colors.

The new cultivar originated from a cross made by the inventor of the proprietary selection of the inventor designated as 89-124, as the male or pollen parent, with the proprietary selection of the inventor designated as 89-031, as the female or seed parent.

The cultivar Hildisco was discovered and selected by the inventor as a flowering plant within the progeny of the stated cross in a controlled environment in Aalsmeer, Holland. Asexual reproduction of the new cultivar by terminal cuttings taken at Aalsmeer, Holland, has shown that the unique features of this new Carnation are stabilized and reproduced true to type in successive generations.

The cultivar Hildisco has not been observed under all possible environmental conditions. The phenotype may vary somewhat with variations in environment such as temperature, daylength and light intensity, without, however, any variance in genotype. The following observations, measurements and comparisons describe plants grown in Palisade, Co., under commercial practice in a polyethylene-covered greenhouse.

The following traits have been repeatedly observed and are determined to be the unique characteristics of Hildisco. These characteristics in combination distinguish Hildisco as a new and distinct cultivar:

1. Medium pink petal color with contrasting dark rose pink eye.
2. Compact growth habit.
3. Freely branching plant habit.
4. Uniform inflorescence display.
5. Very floriferous with numerous flowers per plant.

Compared to its parent, the proprietary selection 89-124, the new Carnation has a bicolor petal color compared to the solid flower color of the selection 89-124. Compared to its parent, the proprietary selection 89-031, the new Carnation is more compact.

The accompanying colored photograph illustrates the overall appearance of the new cultivar, showing the colors as true as it is reasonably possible to obtain in colored reproduction of this type. The photograph comprises a top perspective view of a flowering stem, flower, petals, buds and reproductive organs from a typical potted plant of Hildisco grown in a polyethylene-covered greenhouse in Palisade, Co.

In the following description, color reference are made to The Royal Horticultural Society Colour Chart except where general terms of ordinary dictionary significance are used. Measurements and numerical values represent averages for at least three typical plants grown in 10-cm containers with day temperatures of 24C, night temperatures of 18C, and a light level of 4,500 foot-candles.

Botanical classification: *Dianthus caryophyllus* cultivar Hildisco.

Parentage:

*Male.*—Proprietary selection 89-124.

*Female.*—Proprietary selection 89-031.

Propagation:

*Type cutting.*—Terminal cuttings.

*Time to initiate roots.*—20 days at 21C soil temperature.

*Rooting habit.*—Numerous, fibrous, and well-branched.

Plant description

*Form.*—Compact flowering potted plant, suitable for 10 to 15-cm containers.

*Habit of growth.*—Freely branching, bushy.

*Plant height at flowering.*—Compact, 18 cm.

*Vigor.*—Moderately vigorous, rapid.

*Foliage description.*—Leaves simple, opposite, generally symmetrical, abundant. Size: Length: 6 to 8 cm. Width: 6 mm. Shape: Narrow, lanceolate with acutel leaf tip. Texture: Smooth, glabrous. Margin: Entire. Color: Young foliage top side: 138A. Young foliage under side: 138A. Mature foliage top side: 139A. Mature foliage under side: 138A. Stem color: 139A. Venation: Veins not prominent, inconspicuous.

Flower description:

*Flower type and habit.*—Single flowers that are flat in aspect. Freely and continuously flowering.

*Inflorescences borne.*—Clusters of 4 to 5 flowers on strong peduncles borne above foliage, arising from terminal shoot and leaf axils. Flowers persistent and slightly fragrant.

*Flower longevity.*—14 to 16 days on the plant.

*Flower diameter.*—4.2 cm.

*Flower depth.*—1 cm.

*Flower buds.*—Shape: Cylindrical. Size: Length: 2 cm. Width (diameter): 6 to 8 mm. Opening rate: 4 to 5 days.

*Petals.*—Quantity: 5 to 6. Shape: Fan-shaped. Tip: Finely serrated. Size: Length: 2 cm. Width: 2.2 cm.

Color: Shiny appearance. Outer edge, immature: Medium pink, 68A. Center, immature: Dark rose, 61B. Outer edge, mature: Medium pink, 68A. Center, mature: Dark rose, 61B. Under side: 63C. Fade: Petal color does not fade or discolor.

*Calyx.*—Shape: Cylindrical. Splitting: Not observed. Sepal quantity: 5. Sepal shape: Ovate. Sepal tip: Acute. Sepal size; Length: 7 mm. Width: 8 mm. Sepal color: Outside: 139B. Inside: 139C.

*Peduncle.*—Character: Stiff and upright. Color: Dark green. Length: 10 cm.

*Reproductive organs.*—Stamens: Arranged evenly around ovary. Stamen number: 10 Filament length: 1.8 to 2 cm. Anther color: White. Pollen color: White. Pistils: Single. Style length: 2.5 cm. Stigma color: Pink.

Disease resistance: No known Carnation diseases observed to date.

Seed production: Self-fertile. Fruit is lozenge-shaped and yellowish brown at maturity.

It is claimed:

1. A new and distinct cultivar of Carnation plant named Hildisco, as illustrated and described.

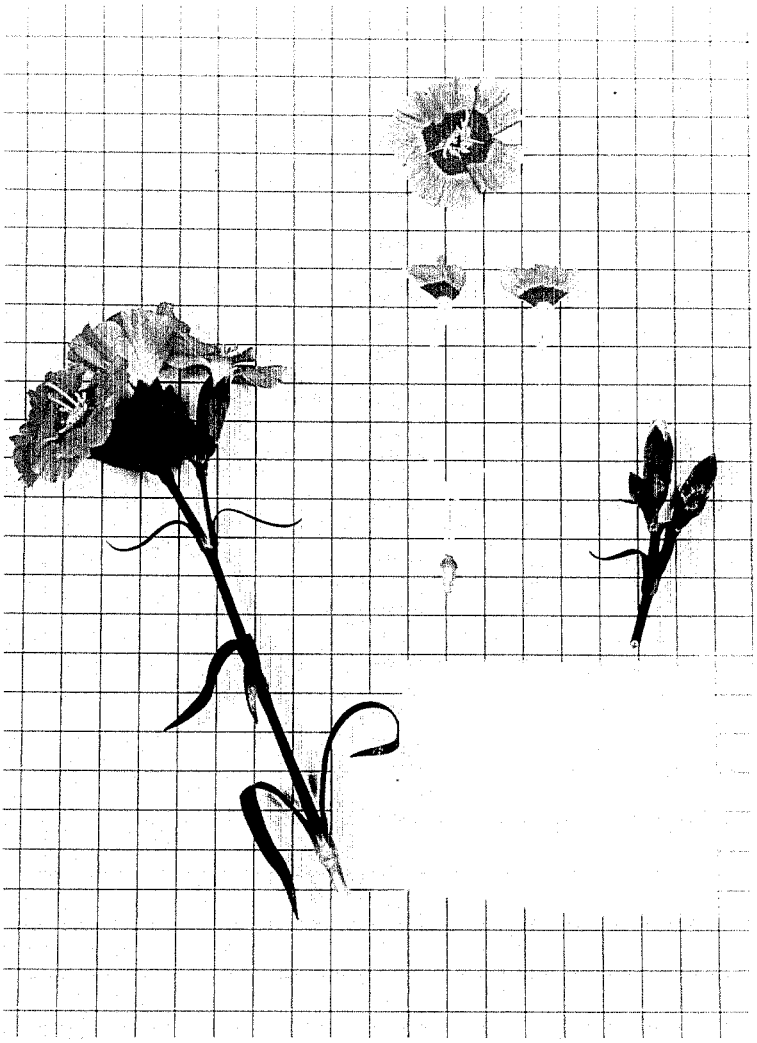

* * * * *